US 6,660,768 B2

(12) United States Patent
Endris et al.

(10) Patent No.: US 6,660,768 B2
(45) Date of Patent: Dec. 9, 2003

(54) PARASITICIDAL COMPOSITIONS AND METHODS OF USE

(75) Inventors: Richard G. Endris, Bridgewater, NJ (US); Wayne B. Rose, deceased, late of Olathe, KS (US); by Shirley Maxine Rose, legal representative, Olathe, KS (US)

(73) Assignee: Schering-Plough Animal Health Corporation, Union, NJ (US)

( * ) Notice: Subject to any disclaimer, the term of this patent is extended or adjusted under 35 U.S.C. 154(b) by 45 days.

(21) Appl. No.: 10/072,267

(22) Filed: Feb. 6, 2002

(65) Prior Publication Data

US 2003/0073667 A1 Apr. 17, 2003

Related U.S. Application Data

(60) Provisional application No. 60/267,373, filed on Feb. 8, 2001.

(51) Int. Cl.[7] .................. A01N 43/08; A01N 53/00; A01N 31/14; A61K 31/34; A61K 31/075
(52) U.S. Cl. .................. 514/468; 514/531; 514/717
(58) Field of Search .................. 514/717, 468, 514/531

(56) References Cited

U.S. PATENT DOCUMENTS

| | | |
|---|---|---|
| 4,020,181 A | 4/1977 | Blackman et al. |
| 5,045,536 A | 9/1991 | Baker |
| 5,236,954 A | 8/1993 | Gladney et al. |
| 5,286,749 A | 2/1994 | Kieran et al. |
| 5,334,585 A | 8/1994 | Derian et al. |
| 5,344,018 A | 9/1994 | Severin |
| 5,449,474 A | 9/1995 | Lucas et al. |
| 5,465,685 A | 11/1995 | Dotolo et al. |
| 5,516,504 A | 5/1996 | Tomlinson |
| 5,942,525 A | 8/1999 | Pennington et al. |
| 6,130,253 A | 10/2000 | Franklin et al. |

*Primary Examiner*—Alton N. Pryor

(57) ABSTRACT

A solvent system for pyrethroids and pyrethrins comprises a terpene or a terpene derivative such as a terpene alcohol, aldehyde or ketone. In a preferred embodiment, the solvent system further comprises an alkylene glycol ether. Compositions comprising pyrethroids and/or pyrethrins in such a solvent system do not crystallize at cold temperatures and have increased efficacy compared to formulations containing conventional solvents.

21 Claims, No Drawings

PARASITICIDAL COMPOSITIONS AND METHODS OF USE

REFERENCE TO RELATED APPLICATIONS

This application claims the benefit of U.S. Provisional Application Serial No. 60/267,373 filed Feb. 8, 2001.

FIELD OF THE INVENTION

The invention relates to compositions for controlling ectoparasites. Specifically, the invention provides parasitical pyrethroid- and pyrethrin-containing formulations comprising solvent systems containing glycol ethers and/or terpenes.

BACKGROUND OF THE INVENTION

Pyrethrins are natural compounds extracted from tropical strains of chrysanthemum flowers (*Pyrethrum cinerariaefolium*). Pyrethroids are synthetic analogs of pyrethrins. Both pyrethrins and pyrethroids have been used as insecticides for controlling ectoparasites (e.g., fleas, flies and ticks) infestations on animals as described e.g., U.S. Pat. No. 4,020,181. A preferred pyrethroid for this purpose is permethrin.

For purpose of administration, the pyrethroid or pyrethrin typically is formulated in a liquid carrier and then applied topically to an animal in need of relief from fleas or other ectoparasites. Desirable carrier substances are solvents that can be mixed with the active agent to provide formulations that can be poured onto an animal. Carriers substances for pyrethroids and pyrethrins have included, for example, aromatic petroleum products such as xylene and toluene, cyclohexamine, alcohols, corn oil, eucalyptus oil and alkyl glycol ethers. While most prior art pyrethroid-containing insecticidal formulations contain only up to 50% by weight of pyrethroid, U.S. Pat. No. 5,236,954 discloses pyrethroid formulations, in particular permethrin formulations, containing permethrin concentrations greater than 50% by using an alkyl glycol ether such as diethylene glycol monomethyl ether. An insecticidal composition having such a high concentration of active ingredient allows for small, easily applied and yet effective doses.

Concentrations of more than 50% by weight active ingredients make topical application more convenient and more aesthetically acceptable. The higher the concentration, the smaller the dose for effective ectoparasite control. A small dose can be applied to a relatively small region of the skin, thus preventing the host from being covered with solvent. This formula and method of application is particularly useful for treating domestic companion animals such as dogs because the animal will not drip solvent or feel sticky when petting occurs immediately after application. Such small doses can be applied without the treated animal being made aware thus easing administration. Although the composition is applied as one or more small doses to a localized region on the animal, the pyrethroid translocates to effectively control ectoparasite infestation over relatively all of the animal. Formulations containing more than 50% by weight of a pyrethroid thus obtain many advantages not present in formulations having a maximum concentration of only up to 50% by weight of the total formulation.

With a larger concentration of active ingredient, such as for example a 65% or greater solution of permethrin, there is not a large amount of solvent present in the formulation, and it has been discovered that pyrethroids and pyrethrins can crystallize out of solution at lower temperatures, e.g., below about 20° C. This is problematic, as it means that the concentration of the pyrethroid or pyrethrin in solution and available for administration to the animal is lessened. Accordingly, there is a need for a solvent system that prevents or minimizes the crystallization of pyrethroids or pyrethrins at lower temperatures.

There is also a need to develop formulations that have a longer period of efficacy than is available from products currently on the market. Products that are efficacious for longer periods of time obviously are desirable as they are more cost effective and will require fewer applications over time to provide effective protection.

SUMMARY OF THE INVENTION

The present invention fulfills this need by providing materials and methods for controlling ectoparasite infestations.

One aspect of the invention provides a parasiticidal composition for topical application to an animal that comprises a pyrethroid or a pyrethrin and a carrier, wherein said carrier comprises a terpene, such as d-limonene. In another embodiment of the invention, the carrier also comprises an alkyl glycol ether. Preferred alkyl glycol ethers include propylene glycol monomethyl ether, dipropylene glycol monomethyl ether, and/or diethylene glycol monomethyl ether. Particularly preferred compositions contain a pyrethroid or pyrethrin in an amount greater than 50% by weight of the total composition. Even more preferred are compositions containing a pyrethroid or pyrethrin in an amount at least about 65% by weight of the total composition. Preferably the pyrethroid is permethrin.

DETAILED DESCRIPTION OF THE INVENTION

All references cited herein are hereby incorporated in their entirety by reference.

The invention provides compositions for controlling ectoparasites that can be found on animals, in particular domestic animals including dogs and cats, but also horses, as well as on food-producing animals such as cattle, sheep and swine. The compositions can be used to treat ectoparasites including fleas, ticks, mange, mites, mosquitoes, nuisance and biting flies, lice, anthropod vectors of disease, as well as internal parasites, e.g., heartworms, hookworms and helmiths.

The compositions of the invention comprise a pyrethroid or a pyrethrin and a carrier comprising a terpene or terpene derivative or a combination of a terpene or terpene derivative and another carrier such as an alkyl glycol ether. Surprisingly, it has been found that when a terpene, such as d-limonene (CAS #5989-27-5), is used as the carrier, crystallization can be minimized and/or avoided. In a preferred embodiment, the carrier comprises a combination of a terpene and propylene glycol monomethyl ether, or a combination of a terpene and dipropylene glycol monomethyl ether (CAS #107-98-2). Preferably the composition comprises from about 30% to about 70% by weight of the terpene or the terpene-alkyl glycol ether combination.

Pyrethroids that can be used to practice the invention include permethrin, phenothrin, acrinathrin, allethrin, bioallethrin, bifenthrin, bioresmethrin, cycloprothrin, cypermethrin, cyhalothrin, lambda cyhalothrin, cyfluthrin, cyphenothrin, tralomethrin, tralocythrin, deltamethrin, empenthrin, fenpropathrin, kadethrin, prallethrin, pyrethrins, resmethrin, sluvalinate, tefluthrin, tetramethrin, transfluthrin, fluvinate, flumethrin and fenvalerate. The most preferred pyrethroid for use in this invention is permethrin (CAS #52645-53-1). Permethrin has a molecular weight of 391.28 grams/mole and technical permethrin comprises from about 25 to 80% cis isomer and from about 20 to 75% trans isomer by weight. In the insecticidal composition of the invention, technical permethrin is suitable and it preferably has a minimum amount of the trans isomer of about 45% by weight and a minimum amount of cis isomer of about 35% by weight.

The ectoparasiticide compositions according to the invention, the concentration of permethrin or other pyrethroid typically is from about 30 about 95% by weight, with preferred level being at least about 45%, even more preferred from 50–75% (by weight). The remaining portion of the composition is the carrier substance.

In addition to d-limonene, other terpenes suitable for use in the claimed invention include (α-pinene, β-pinene, β-myrcene and terpinolene. In addition, terpene derivatives, or terpenoids, may also be used as the carrier or as one component of the carrier. As used herein, the terms "terpene derivative" or "terpenoid" include terpene alcohols such as geraniol, terpineol and linalool, terpene aldehydes such as citronellal, and terpene ketones such as pulegone, all of which are suitable for use as the carrier or as one component of the carrier in the compounds of the claimed invention.

The terpene, or the terpene alcohol, aldehyde or ketone, can be used as the sole liquid carrier in the compositions of this invention. Alternatively, the carrier can comprise a combination of the terpene or terpene derivative and another carrier, such as hexylene glycol or an alkyl glycol ether. Preferred alkyl glycol ethers include propylene glycol monomethyl ether, dipropylene glycol monomethyl either and diethylene glycol methyl ether. If a mixture of terpene or terpene derivative and alkyl glycol ether is used, the mixture desirable contains at least 10% by weight of the terpene component. Preferably, the ratio of terpene to alkyl glycol ether is from about 3:1 to about 1:3. More preferably, the ratio of terpene to alkyl glycol ether is from about 2:1 to about 1:2. Other conventional carriers can also be used in combination with the terpene or terpene derivative.

The compositions of the present invention are effective against ectoparasites while remaining non-irritating and non-toxic to the host. Inasmuch as the compositions can be formulated with a high concentration of active ingredient they can be easily applied in small yet effective doses. A particularly effective method of application consists of applying the composition to one or more localized regions on the host, such as by applying a small spot of the composition on an animal at the region between its shoulder blades. Larger animals can be treated with a second small spot of the composition at the rump region. It is believed that the pyrethroid component translocates within a relatively short period of time to effectively cover the entire surface of the host's body. No special expertise is required to apply the treatment so animal owners may do so without the assistance of a health care professional and without special equipment.

Other inert ingredients can be added to the present composition, as desired. Such ingredients include spreading agents, synergists, attractants, repellents, adhesion promoters, surface active agents, stabilizers, skin conditioners, perfumes, odor masking agents, taste deterrants, coat sheeners and coloring agents. Additional active ingredients, such as other insecticides and insect growth regulators can also be included in the composition of the present invention.

Suitable spreading agents are liquids that distribute themselves particularly readily on the skin. Isopropyl myristate is commonly used spreading agent. The desirable properties of spreading agents, sometimes referred to as spreading oils, are generally well known to those skilled in the art. Attractants include pheromones such as 2,6-dichlorophenol. Repellents include citronellol, diethyl toluimide, dimethyl phthalate, and the like.

Of the other inert ingredients that can be utilized with the present invention there are adhesion promoters. Adhesion promoters include carboxymethyl-cellulose, methylcellulose and other cellulose derivatives and starch derivatives, polyacrylates, alginates, gelatin, gum arabic, polyvinylpyrrolidone, polyvinyl alcohol, copolymers of methyl vinyl ether and maleic anhydride, polyethylene glycols, paraffins, oils, waxes and hydrogenated castor oil, colloidal silicic acid or mixtures of these substances.

The compositions of the present invention do not normally contain surface active agents, but these may be included if desired. Surface active agents (comprising emulsifiers and wetting agents) include (i) anionic surface active agents, such as sodium lauryl sulfate, fatty alcohol ethersulfates and monoethanolamine salts of mono-dialkylpolyglycol ether orthophosphoric acid esters, (ii) cationic surface active agents, such as cetyltrimethylammonium chloride, (iii) amphophilic surface active agents, such as di-sodium-N-lauryl-amino-diproprionate or lecithin, and (iv) non-ionic surface active agents, for example, polyoxyethylated castor oil, polyoxyethylated sorbitane monoleate, sorbitan monostearate, ethyl alcohol, glycerol monostearate, polyoxyethylene stearate and alkylphenol polyglycol ethers.

For preventing chemical degradation that occurs in the case of some active compounds, stabilizers may also be used and include, for example, antioxidants such as tocopherols, butyl-hydroxyanisole, butylhydroxytoluene and carbodiimides, e.g., 2,2-6,6-tetraisopropyldiphenylcarbodiimide), and scavengers such as epichlorhydrin. Coloring agents include conventional dyes that are soluble in the carrier of the present invention, such as Sudan Red or Oil Golden Yellow.

In order to prepare the insecticidal composition of the present invention, a pyrethroid is heated to 65–80° C. until any crystals present are liquefied. The liquid is then mixed until uniform. A liquid carrier solvent is placed into a separate unheated vessel. The permethrin is then added to the vessel. The permethrin and carrier solvent are then mixed to uniformity. Additives, such as those listed above (e.g., skin conditioners, perfumes, coat sheeners, and spreading agents), may also be included in the vessel and mixed into the formulation.

In the preferred embodiment of this invention, permethrin is heated to about 65° C. A 2:1 to 1:2 mixture of d-limonene and propylene glycol monomethyl ether is placed in a clean tank and the permethrin added and mixed until uniform. After the permethrin has been formulated into this simple liquid mixture, the mixture may serve as a starting point for the formulation of topical preparations in other physical states. For instance, gelling agents may be added to create topical preparations in the form of gels and sols. Gases may be added to create topical preparations that can be delivered as aerosols. Other formulating agents may be added to the liquid mixture to create ointments and pastes.

The insecticidal composition of the present invention is suitable for use on most mammals including humans, horses, cattle, giraffes and domesticated companion animals such as dogs. Because it is so non-toxic, it may be used on young animals, e.g., 3 weeks of age, as well as adult animals. It is also effective against a variety of parasites including ticks, fleas, flies, keds, and mites.

The composition according to the present invention is particularly useful for horses and other large mammals because the doses required are much smaller as compared to the pyrethroid compositions of 50% by weight or lesser concentrations. The insecticidal composition of this invention is useful for the control of arthropods, insects and acarine ectoparasites such as fleas, ticks, flies, keds, and mites. Its most preferred use is for the control of ticks and fleas on dogs.

The composition may be applied to the host animal by any conventional method for the localized application of compositions, for example by dropping a small volume of liquid composition on the mammal's body. One advantage of the use of a highly concentrated composition is that only a small volume is necessary. The composition applied in this manner appears to exhibit migration, wherein the pyrethroid component is translocated to other regions on the animal body. This migration or spreading effect enables administration of the pyrethroid to relatively all of the animal body surface for ectoparasitic control.

Formulations with pyrethroid concentrations in excess of 50% by weight can be packaged in a single dose package. For example, a single 1 cubic centimeter (cc) dose of a liquid formulation comprised of permethrin and solvent ethanol can be packaged in a collapsible 1 cc tube. Because the formulation avoids the use of strong organic solvents like xylene, cyclohexanone, and toluene, there is greater choice of tube material. Single dose containers make storage and disposal more convenient for animal owners. Multiple dose liquid formulations can be packaged in containers of more than 1 cc capacity. The high concentration composition also decreases container size requirements for multiple dose containers as well as the container size requirements for single dose containers for larger animals. A package assembly of the type described in U.S. Pat. No. 5,344,018 can conveniently be used.

Since the composition has a high concentration of pyrethroid, this small application of a spot or line on the animal will effectively control insect and arachnid parasite infestations on mammals from within three to twenty four hours post administration and for up to four weeks post administration. This method is non-toxic and the concentrated composition does not irritate the animals skin. While a necessary amount of the composition of the present invention needed to be applied for effective insecticidal activity depends upon the size of the animal and the precise concentration and delivery capabilities of the particular composition, a 1 cubic centimeter (cc) volume of the preferred liquid composition has been found to be effective on dogs weighing less than 15 kg. A 1 to 2 milliliter volume of the preferred 65% by weight permethrin delivers 65–130 mg permethrin. On dogs larger than 15 kg, it has been found to be effective to apply 1 cc of 65% by weight permethrin composition between the shoulder blades in conjunction with another 1 mL at the tailhead. In a preferred embodiment, for every kilogram of the host body weight, about 33 or more milligrams of the composition should be applied.

The present invention is more particularly described in the following examples which are intended as illustrative only since numerous modifications and variations therein will be apparent to those skilled in the art.

EXAMPLES

Example 1

| Ingredient | A % wt. | A Quantity (g) | B % wt. | B Quantity (g) |
|---|---|---|---|---|
| permethrin (0.955% pure) | 65.00 | 680.63 | 65.00 | 680.63 |
| d-limonene | 35.00 | 319.37* | 11.55 | 115.50 |
| propylene glycol monomethyl ether | — | — | 23.45 | 203.87* |
| | 100.00 | 1000.00 | 100.00 | 1000.00 |

*The products were formulated at 100% of the active ingredient. Adjustments for purity were made with the major inert of the product.

Permethrin was charged to the container, followed by the solvent ingredient(s). Stirring was then begun, and continued for five minutes, or until the solution appeared uniform, with warming as necessary to solubilize the permethrin. The contents of the container were packaged into glass containers, sealed, and labeled appropriately.

Example 2

| Ingredient | A % wt. | A Quantity (g) | B % wt. | B Quantity (g) | C % wt. | C Quantity (g) |
|---|---|---|---|---|---|---|
| permethrin (0.946% pure) | 65.00 | 68.71 | 65.00 | 68.71 | 65.00 | 68.71 |
| geraniol | 35.00 | 31.29* | 23.35 | 23.35 | 17.50 | 17.5 |
| propylene glycol monomethyl ether | — | — | 11.65 | 7.95** | 17.50 | 13.79** |
| | 100.00 | 100.00 | 100.00 | 100.00 | 100.00 | 100.00 |

*The product was formulated at 100% of the active ingredient. Adjustment for purity was made with geraniol.
**These products were formulated at 100% of the active ingredient. Adjustments for purity were made with propylene glycol monoethyl ether.

These formulas were prepared by the method of Example 1.

Example 3

Studies were conducted to see whether certain solvent or solvent mixture that had better solvent properties for permethrin than methyl carbitol.

Several solvent types were evaluated. Those solvents that appeared to have good solubility at refrigerator [4° C.] and freezer temperatures [−10° C.] were chosen for evaluation, as were solvents that have been accepted by the EPA for use on animals (40 C.F.R. §180.1001(e)).

| Solvent Evaluated | Source |
|---|---|
| Hexylene glycol [2-methyl-2,4-pentanediol] | Shell Chemical |
| Methyl Carbitol ® [diethylene glycol monomethyl ether] | Union Carbide |
| Dowanol ® PM [propylene glycol monomethyl ether] | Dow Chemical |
| Dowanol ® DPM [dipropylene glycol monomethyl ether] | Dow Chemical |

-continued

| Solvent Evaluated | Source |
|---|---|
| d-Limonene [1-methyl-4-isopropenyl-1-cyclohexene] | Florachem Corp. |

Solvents were obtained from their basic manufacturer or through Ashland Chemical.

In each of the following Examples 3A-3D, permethrin was dissolved in the solvent or solvent mixtures according to the method of Example 1. These solutions were poured into 100 mL tubes with screw top caps. These tubes were placed in the cold water bath and allowed to come to equilibrium at the temperature of the bath. After the solutions had reached equilibrium in the bath, the preparations were seeded with crystals of permethrin. The seeded preparations were then thoroughly shaken, replaced in the bath and allowed to remain in the bath for a 24 hour period. The preparations were then examined for crystallization, then again thoroughly agitated and replaced in the bath for an additional time period. Samples of the supernatant were removed after additional crystallization had occurred. The supernatant samples were analyzed for their permethrin concentration and the trans/cis isomer ratio.

Example 3A

To determine the relative solubility of permethrin in the different solvents, a cold temperature bath was obtained, and was set initially at 25° C. (The water bath contained a mixture of ethylene glycol and water but had a freeze point below −15° C.)

The original solutions of permethrin were made to be 70% permethrin. Compensation was made for the purity of the permethrin, so the typical ratio of technical permethrin to solvent was 74.3% permethrin to 25.7% solvent, by weight.

When no crystallization occurred, additional permethrin was charged to the solution to bring the permethrin concentration to 75% and the temperature of the bath was lowered to 20° C. At both temperatures, the solutions were seeded with crystals of permethrin. After 24 hours the tubes were examined for the relative amount of crystallization that may have occurred in each of the solutions. Where crystallization had occurred, samples of the supernatant were pulled from the vials and the temperature of the bath was lowered to 15° C.

The samples were analyzed to determine the concentration of permethrin and the trans/cis isomer ratios. When some of the samples became completely solid at 15° C., the temperature of the bath was raised to 17.5° C. Samples were again taken for assay from the solutions of hexylene glycol and methyl Carbitol® (diethylene glycol monomethyl ether). The results of the initial study (Table 1) demonstrated that d-limonene was the superior solvent for permethrin in that there were less crystals in the d-limonene solutions. The solvents propylene glycol monomethyl ether and dipropylene glycol monomethyl ether had better solubility than methyl Carbitol® for permethrin. These two glycol ethers demonstrated good solubility for permethrin, but propylene glycol monomethyl ether had fewer crystals in the low temperature studies than dipropylene glycol monomethyl ether (Table 3).

TABLE 1

| Temperature | Permethrin | Trans Isomer | Cis Isomer | Trans/Cis Ratio | Comments |
|---|---|---|---|---|---|
| d-limonene | | | | | |
| Initial | 70.43% | 40.89% | 29.54% | 1.38 | No crystallization occurred at 25° C., so an additional 5% permethrin was charged to the product. Crystallization still did not occur so permethrin crystals were added to the solution twice at 25° C. and then once at 20° C. At the lowest temperature, 15° C. crystals remained in the solution. |
| 25° C. | 75.29% | 43.76% | 31.53% | 1.39 | |
| 20° C. | 74.84% | 43.37% | 31.47% | 1.38 | |
| 17.5° C. | NA | NA | NA | NA | |
| 15° C. | NA | NA | NA | NA | |
| Hexylene Glycol | | | | | |
| Initial | 71.09% | 41.32% | 29.77% | 1.39 | No crystallization occurred at 25° C., so an additional 5% permethrin was charged to the product. Crystallization still did not occur so permethrin crystals were added to the solution twice at 25° C. Crystals remained in the solution at 25° after the second addition of the permethrin crystals. The solution completely solidified at 20°. Samples were pulled after tubes were held for 24 hours at 17.5° C. The product was mostly solid at 17.5° C. The product was solid at 15° C. |
| 25° C. | 75.02% | 43.67% | 31.35% | 1.39 | |
| 20° C. | NA | NA | NA | NA | |
| 17.5° C. | 74.37% | 48.47% | 25.90% | 1.87 | |
| 15° C. | NA | NA | NA | NA | |
| Dipropylene Glycol Monomethyl Ether | | | | | |
| Initial | 70.35% | 40.94% | 29.41% | 1.39 | No crystallization occurred at 25° C., so an additional 5% permethrin was charged to the product. Crystallization still did not occur, so permethrin crystals were added to the solution twice |
| 25° C. | 75.39% | 43.74% | 31.66% | 1.38 | |
| 20° C. | 75.15% | 43.60% | 31.55% | 1.38 | |
| 17.5° C. | NA | NA | NA | NA | |
| 15° C. | 73.83% | 43.79% | 30.03% | 1.46 | |

TABLE 1-continued

| Temperature | Permethrin | Trans Isomer | Cis Isomer | Trans/Cis Ratio | Comments |
|---|---|---|---|---|---|
| | | | | | at 25° C. Crystals remained in the solution at 25° C. after the second addition of permethrin crystals. The product became solid at 15° C. No assay was made at this temperature. |
| | | Propylene Glycol Monomethyl Ether | | | |
| Initial | 70.78% | 40.22% | 29.55% | 1.40 | No crystallization occurred at |
| 25° C. | 75.66% | 43.88% | 31.79% | 1.38 | 25° C., so an additional 5% |
| 20° C. | 74.84% | 43.78% | 31.06% | 1.41 | permethrin was charged to the |
| 17.5° C. | NA | NA | NA | NA | product. Crystallization still did |
| 15° C. | 74.85% | 43.54% | 31.31% | 1.39 | not occur so permethrin crystals were added to the solution twice at 25° C. and then once at 20° C. At the lower temperature, crystals remained in the solution. The product was mostly solid at 15° C., but there was enough liquid to pull a sample for assay. |
| | | Diethylene Glycol Monomethyl Ether | | | |
| Initial | 69.70% | 40.91% | 28.79% | 1.42 | No crystallization occurred at |
| 25° C. | 74.90% | 43.56% | 31.34% | 1.39 | 25° C., so an additional 5% |
| 20° C. | 75.02% | 43.81% | 31.22% | 1.40 | permethrin was charged to the |
| 17.5° C. | 74.44% | 45.73% | 28.71% | 1.59 | product. Crystallization still did |
| 15° C. | NA | NA | NA | NA | not occur, so permethrin crystals were added to the solution twice at 25° C. Crystals remained in the solution at 25° C. after the second addition of permethrin crystals. The solution showed quite a bit of crystallization at 20° C. and at 15° C. it became solid. The product was sampled after being held at 17.5° C. for 24 hours. The product was mostly solid. No sample was taken at the 15° C. temperature. |

Example 3B

After the relative solubility of permethrin in the various neat solvents had been determined, a second study was initiated to determine if a mixture of the better solvents would enhance the solubility of permethrin in solution. The solvent mixtures tested were: dipropylene glycol monomethyl ether/d-limonene and propylene glycol monomethyl ether/d-limonene.

These solvent mixtures were evaluated at ratios of 2:1, 1:1, 1:2, and then at 8:2 and 9:1 (the first number refers to one of the glycol ethers, the second number refers to d-limonene). The concentration of the permethrin in these mixtures was varied from 55% to 75% permethrin w/w. In all cases, the purity of the permethrin was taken into consideration, so that actual concentration of pure permethrin was at the percentages given above.

These solutions of permethrin were placed in a water bath at low temperatures (0, 5, 10, 20 and 25° C.) and seeded. This resulted in saturated solutions of permethrin in the given solvent mixture at that particular temperature. These data then were used to determine the formulation with the best low temperature solubility of permethrin.

The mixed solvent studies [Tables 2 through 5] revealed that the mixtures of d-limonene with either of the glycol ethers resulted in solutions in which permethrin had better solubility at low temperatures than in any single solvent in this study. The data also showed that as the temperature was lowered, the amount of the cis isomer that remained in solution was greater in solvent mixtures of d-limonene and propylene glycol monomethyl ether and d-limonene and dipropylene glycol monomethyl ether than any of these solvents alone.

TABLE 2

Solubility of permethrin in Propylene glycol monomethyl ether [PM] and Diethylene glycol monomethyl ether [DM].

| Original % permethrin | PM | | | DM | | |
|---|---|---|---|---|---|---|
| | % permethrin remaining in solution | 25° C. trans/cis isomer ratio | Crystals** | % permethrin remaining in solution | 25° C. trans/cis isomer ratio | Crystals |
| 50 | 51.28 | 1.28 | None | 49.43 | 1.24 | None |
| 55 | 56.19 | 1.28 | None | 53.98 | 1.23 | None |
| 60 | 60.99 | 1.24 | None | 61.10 | 1.22 | None |
| 65 | 66.71 | 1.22 | None | 64.25 | 1.25 | None |
| 75 | 75.82 | 1.21 | None | 74.53 | 1.30 | None |

| Original % permethrin | % permethrin remaining in solution | 20° C. trans/cis isomer ratio | Crystals | % permethrin remaining in solution | 20° C. trans/cis isomer ratio | Crystals |
|---|---|---|---|---|---|---|
| 50 | 50.60 | 1.28 | None | 50.55 | 1.24 | None |
| 55 | 55.54 | 1.29 | None | 55.14 | 1.23 | None |
| 60 | 61.27 | 1.25 | None | 60.05 | 1.31 | None |

TABLE 2-continued

Solubility of permethrin in Propylene glycol monomethyl ether [PM] and Diethylene glycol monomethyl ether [DM].

| 65 | 66.25 | 1.23 | None | 64.85 | 1.31 | None |
| 75 | 76.84 | 1.23 | None | 74.20 | 1.39 | Crystals |

| Original % permethrin | % permethrin remaining in solution | 10° C. trans/cis isomer ratio | Crystals | % permethrin remaining in solution | 10° C. trans/cis isomer ratio | Crystals |
|---|---|---|---|---|---|---|
| 50 | No Assay | No Assay | None | 46.80 | 1.82 | 1/4 |
| 55 | No Assay | No Assay | Few | 50.72 | 2.08 | 1/2 |
| 60 | 59.08 | 1.51 | 1/3 | 56.17 | 1.97 | 2/3 |
| 65 | 61.63 | 1.99 | 1/2 | No Assay | No Assay | 2/3 |
| 75 | 72.22 | 2.05 | 2/3 | No Assay | No Assay | 3/4 |

| Original % permethrin | % permethrin remaining in solution | 5° C. trans/cis isomer ratio | Crystals | % permethrin remaining in solution | 5° C. trans/cis isomer ratio | Crystals |
|---|---|---|---|---|---|---|
| 50 | 46.61 | 1.77 | None | 46.00 | 1.90 | 1/4 |
| 55 | 52.71 | 1.60 | Few | 51.74 | 1.82 | 1/2 |
| 60 | 56.69 | 1.94 | 1/3 | 55.09 | 2.24 | >90% |
| 65 | 61.50 | 1.98 | 1/2 | 60.22 | 2.26 | >90% |
| 75 | 70.89 | 2.21 | >90% | No Assay | No Assay | >90% |

TABLE 3

Solubility of permethrin in mixtures of glycol ethers/d-limonene at 0° C.

| % d-limonene of solvent mixture | % Trans Isomer | % Cis Isomer | % Total Permethrin | Isomer Ratio Trans/Cis |
|---|---|---|---|---|
| *70% permethrin in PM\*/d-limonene* | | | | |
| 100% | 47.35 | 17.26 | 64.61 | 2.74 |
| 67% | 46.85 | 18.51 | 65.94 | 2.50 |
| 50% | 47.10 | 18.84 | 65.36 | 2.53 |
| 33% | 48.05 | 17.15 | 65.20 | 2.80 |
| 0% | 41.31 | 16.60 | 57.91 | 2.49 |
| *65% permethrin in PM\*/d-limonene* | | | | |
| 100% | 42.85 | 17.42 | 60.27 | 2.46 |
| 67% | 42.56 | 18.89 | 61.45 | 2.25 |
| 50% | 42.04 | 19.70 | 61.74 | 2.13 |
| 33% | 42.89 | 16.53 | 59.42 | 2.60 |
| 0% | 38.96 | 13.70 | 52.65 | 2.85 |
| *70% permethrin in DPM\*\*/d-limonene* | | | | |
| 100% | 47.35 | 17.26 | 64.61 | 2.74 |
| 67% | 46.28 | 19.77 | 66.05 | 2.34 |
| 50% | 46.47 | 19.19 | 65.66 | 2.42 |
| 33% | No Data | No Data | No Data | No Data |
| 0% | 48.53 | 15.71 | 64.24 | 3.09 |
| *65% permethrin in DPM\*\*/d-limonene* | | | | |
| 100% | 42.85 | 17.42 | 60.27 | 2.46 |
| 67% | 41.62 | 19.77 | 61.33 | 2.11 |
| 50% | 42.64 | 18.91 | 61.55 | 2.26 |
| 33% | 42.48 | 19.17 | 61.65 | 2.22 |
| 0% | 43.33 | 14.92 | 58.25 | 2.90 |

TABLE 4

Solubility of permethrin in mixtures of glycol ethers/d-limonene at 5° C.

| % d-limonene of solvent mixture | % Trans Isomer | % Cis Isomer | % Total Permethrin | Isomer Ratio Trans/Cis |
|---|---|---|---|---|
| *70% permethrin in PM\*/d-limonene* | | | | |
| 100% | 45.98 | 20.06 | 66.05 | 2.29 |
| 67% | 42.93 | 25.40 | 68.33 | 1.69 |
| 50% | 43.83 | 25.82 | 69.65 | 1.70 |
| 33% | 44.48 | 22.89 | 67.36 | 1.94 |
| 0% | 47.00 | 17.79 | 64.79 | 2.64 |
| *65% permethrin in PM\*/d-limonene* | | | | |
| 100% | 39.89 | 23.33 | 62.73 | 1.71 |
| 67% | 38 | 26.13 | 64.86 | 1.48 |
| 50% | 73 | 24.22 | 64.05 | 1.65 |
| 33% | 39.82 | 22.53 | 63.08 | 1.8 |
| 0% | 40.55 | 16.24 | 59.51 | 2.66 |
| *70% permethrin in DPM\*\*/d-limonene* | | | | |
| 100% | 45.98 | 20.06 | 66.05 | 2.29 |
| 67% | 43.23 | 26.15 | 69.38 | 1.65 |
| 50% | 43.33 | 25.16 | 68.48 | 1.72 |
| 33% | 44.17 | 24.98 | 69.64 | 1.77 |
| 0% | 47.52 | 18.04 | 65.56 | 2.64 |
| *65% permethrin in DPM\*\*/d-limonene* | | | | |
| 100% | 39.89 | 23.33 | 62.73 | 1.71 |
| 67% | 38.43 | 27.11 | 65.55 | 1.42 |
| 50% | 39.36 | 25.47 | 64.83 | 1.55 |
| 33% | 39.40 | 24.52 | 63.92 | 1.61 |
| 0% | 42.89 | 17.64 | 60.53 | 2.43 |

TABLE 5

Solubility of permethrin in mixtures of glycol ethers/d-limonene at 10° C.

| % d-limonene of solvent mixture | % Trans Isomer | % Cis Isomer | % Total Permethrin | Isomer Ratio Trans/Cis |
|---|---|---|---|---|
| *70% permethrin in PM\*/d-limonene* | | | | |
| 100% | 41.18 | 28.12 | 69.30 | 1.46 |
| 67% | 43.87 | 25.17 | 69.04 | 1.74 |
| 50% | 44.59 | 23.82 | 68.40 | 1.87 |
| 33% | 45.07 | 22.74 | 67.80 | 1.98 |
| 20% | 45.56 | 22.76 | 66.92 | 1.94 |
| 10% | 45.66 | 21.04 | 66.70 | 2.17 |
| 0% | NA | NA | NA | NA |
| *65% permethrin in PM\*/d-limonene* | | | | |
| 100% | 38.32 | 27.56 | 65.88 | 1.39 |
| 67% | 38.14 | 27.82 | 65.95 | 1.37 |
| 50% | 38.95 | 25.51 | 64.45 | 1.53 |
| 33% | 40.13 | 23.77 | 63.89 | 1.70 |
| 20% | 39.03 | 25.33 | 64.35 | 1.54 |
| 10% | 40.43 | 21.65 | 62.08 | 1.87 |
| 0% | NA | NA | NA | NA |
| *70% permethrin in DPM\*\*/d-limonene* | | | | |
| 100% | 41.18 | 28.12 | 69.30 | 1.46 |
| 67% | 44.62 | 23.36 | 67.98 | 1.91 |
| 50% | 44.50 | 22.29 | 66.70 | 2.00 |
| 33% | 45.26 | 22.12 | 67.38 | 2.05 |
| 20% | 45.69 | 22.02 | 67.71 | 2.08 |
| 10% | 46.10 | 20.85 | 66.95 | 2.21 |
| 0% | 46.54 | 20.04 | 66.58 | 2.32 |
| *65% permethrin in DPM\*\*/d-limonene* | | | | |
| 100% | 38.32 | 27.56 | 65.88 | 1.39 |
| 67% | 39.43 | 25.50 | 64.92 | 1.55 |
| 50% | 39.27 | 25.04 | 64.30 | 1.60 |
| 33% | 41.55 | 23.39 | 64.93 | 1.78 |

TABLE 5-continued

Solubility of permethrin in mixtures of glycol ethers/d-limonene at 10° C.

| % d-limonene of solvent mixture | % Trans Isomer | % Cis Isomer | % Total Permethrin | Isomer Ratio Trans/Cis |
|---|---|---|---|---|
| 20% | 40.37 | 23.10 | 63.46 | 1.75 |
| 10% | 41.06 | 20.36 | 61.42 | 2.02 |
| 0% | 41.29 | 21.61 | 62.90 | 1.91 |

*PM - propylene glycol monomethyl ether
**DPM - dipropylene glycol monomethyl ether

Example 3C

A third study was initiated to determine if there would be increased solubility of lower concentrations of permethrin in the solvent mixtures. This study was conducted with solvent mixtures of d-limonene and propylene glycol monomethyl ether at −15° C. Solutions of 30% permethrin were prepared in the solvent mixtures of d-limonene and propylene glycol monomethyl ether and placed in the cold temperature bath. The solvent systems used were:

100% d-limonene

2:1 d-limonene/propylene glycol monomethyl ether;

1:1 d-limonene/propylene glycol monomethyl ether;

1:2 d-limonene/propylene glycol monomethyl ether;

1:4 d-limonene/propylene glycol monomethyl ether; and

100% propylene glycol monomethyl ether.

The temperature was regulated to −15° C. The solutions were placed in the bath and allowed to crystallize and reach equilibrium. The supernatant solution was sampled and analyzed to determine the concentration of permethrin and isomer ratio.

The results of this study (Table 6), show that the solubility phenomenon observed with permethrin concentrations greater than 50% was also observed at this initial concentration of 30% permethrin at −15° C. That is, there is an increased solubility of the cis isomer in the mixed solvents when compared to the same initial concentration with either of the solvents alone at the lower temperature of 31 15° C. This increase of the cis isomer gives rise to an increase in the overall solubility of permethrin in these solvent mixtures, even though the overall solubility of permethrin at this temperature was shown to be less than the initial 30%.

TABLE 6

| % d-limonene in formula | % permethrin in solution | Isomer Ratio Trans/Cis |
|---|---|---|
| 100 | 25.93 | 2.05 |
| 67 | 27.51 | 1.66 |
| 50 | 27.20 | 1.75 |
| 33 | 25.52 | 2.05 |
| 20 | 24.78 | 2.33 |
| 0 | 23.57 | 2.83 |

Example 3D

The purpose of this study was to determine the solubility of permethrin at 20° C. A 70% solution permethrin in propylene glycol monomethyl ether was prepared. The technical permethrin and original 70% solution were sampled for determination of permethrin concentration and the trans/cis ratio. The solution was placed in the bath, and continually stirred. The bath temperature was lowered to 0° C. After crystallization occurred in the solution, the bath temperature setting was raised to 20° C. and the stirred slurry was allowed to equilibrate over a three-day period. After this time, samples of the supernatant were pulled on consecutive days. The crystals were separated from the liquid layer by filtration, and the crystals were washed with petroleum ether. All resulting samples, of both supernatant and crystals, were analyzed for both total permethrin content and the trans/cis isomer ratio. The crystals were washed to remove any residual solution that might contaminant their analysis.

The results of the study are shown in Table 7. These data show that permethrin has good solubility in propylene glycol monomethyl ether. However, as with all solutions of permethrin that have been observed, the cis isomer will crystallize and precipitate from solution if the temperature is low enough. The result of this experiment indicates that permethrin has a solubility of greater than 70% at 20° C., but the isomer ratio shifts in favor of the trans isomer, with the cis isomer coming out of solution at this temperature.

TABLE 7

| | % Permethrin | Isomer Ratio Trans/Cis |
|---|---|---|
| Assay of Technical Permethrin | 96.89 | 1.34 |
| Initial Assay of 70% Solution | 72.86 | 1.34 |
| Assay after Equilibrium Reached | 72.93 | 1.41 |
| 2nd Day after Equilibrium Reached | 72.96 | 1.41 |
| Assay of Crystals | 100% as the cis isomer | 0 |

The results of Examples 3A-3D at low temperatures, demonstrates that permethrin shows the greatest solubility in d-limonene. The order of decreasing solubility in the tested solvents was:

(a) d-limonene (b) propylene glycol monomethyl ether (c) dipropylene glycol monomethyl ether (d) diethylene glycol monomethyl ether (e) 2-methyl-2,4-pentanediol (hexylene glycol)

The permethrin cis isomer demonstrated an unusual and unexpected increase in solubility at temperatures in the mixed solvent systems. At concentrations less than 50%, permethrin continued to show increased solubility in mixed solvents, as compared to its solubility in the same solvents individually.

Permethrin was soluble in propylene glycol monomethyl ether at a level greater than 70%, but the cis isomer crystallized at 0° C. and remained crystalline at 20° C. at a concentration of about 70% permethrin in solution.

The trans isomer of permethrin has a very high solubility in the selected solvents. The cis isomer has increased solubility in the solvent mixtures when compared to the solutions of neat solvents.

Example 4

The efficacy of 65% permethrin was evaluated in 5 solvents or solvent mixtures. Six dogs (3<15 kg and 3≧15 kg) were randomly assigned to each of the following 7 treatment groups.

| Treatment Group | Formulation |
|---|---|
| 1 | 65% permethrin in d-limonene. |
| 2 | 65% permethrin in a mixture (2:1) of d-limonene and Dowanol ® PM (propylene glycol monomethyl ether). |

-continued

| Treatment Group | Formulation |
|---|---|
| 3 | 65% permethrin in a mixture (1:1) of d-limonene and Dowanol ® PM. |
| 4 | 65% permethrin in a mixture (1:2) of d-limonene and Dowanol ® PM. |
| 5 | 65% permethrin in Dowanol ® PM. |
| 6 | 65% permethrin in methyl Carbitol ® (Defend EXspot ® Insecticide for Dogs). |
| 7 | Untreated control. |

Each treatment group contained 3 dogs that weighed <15 kg and 3 dogs that weighed ≧15 kg. One treatment application was made to each dog. Each dog that weighed <15 kg received 1.0 mL of a test formulation applied to the skin on the dorsum of the neck. Each dog that weighed >15 kg received 2.0 mL of a test formulation with 1.0 mL applied to the skin on the dorsum of the neck and 1.0 mL applied to the dorsum of the rump.

Fleas (100 unfed, adult cat fleas, *Ctenocephalides felis*) were applied to each dog on Study Days -6, -1, 4, 11, 18, 25 and 32. Ticks (50 unfed, adult *Amblyomma americanum*) were applied to each dog on Study Days -1, 3, 9, 16, 23 and 30. Fleas were counted on Study Days 3, 7, 14, 21, 28, and 35. Ticks were located, counted and removed from the dogs. Thereafter dogs were combed with an extra-fine flea comb and live fleas were removed and counted while combing each dog for at least 5 minutes or until no live fleas or ticks were found.

The individual(s) who performed fleas and tick counts were "blinded" regarding the treatment group to which each dog was assigned. No signs of dermal irritation were observed after treatment with any of the formulations.

Efficacy was determined using Abbott's formula with geometric means:

$$\% \text{ Efficacy} = \frac{\text{Mean \# of parasites per control animal} - \text{Mean \# of parasites per treated animal}}{\text{Mean \# of parasites / control animal}} \times 100$$

The efficacy of the various formulations against *Ctenocephalides felis*, is shown in Table 8.

TABLE 8

| | % Efficacy (Fleas) | | | | | |
|---|---|---|---|---|---|---|
| Solvent | Day 3 | Day 7 | Day 14 | Day 21 | Day 28 | Day 35 |
| d-limonene | 90 | 100 | 100 | 90 | 88 | 49 |
| PM/d-l 1:2 | 95 | 98 | 100 | 96 | 98 | 63 |
| PM/d-l 1:1 | 90 | 99 | 100 | 95 | 97 | 75 |
| PM/d-l 2:1 | 90 | 100 | 99 | 98 | 95 | 81 |
| Dowanol® PM | 94 | 100 | 100 | 99 | 98 | 81 |
| Methyl Carbitol | 89 | 100 | 98 | 96 | 48 | Dropped |
| Control | (81) | (82) | (81) | (80) | (82) | (77) |

PM = Dowanol ® PM (propylene glycol monomethyl ether)
d-l = d-limonene
() - indicates the geometric mean number of parasites/control dog (n = 6)

The formulations that contained Dowanol® PM demonstrated an initial efficacy of 90%–95% within 3 days after treatment. High levels of efficacy (93%–100%) for formulations that contained Dowanol® PM were observed for 28 days after treatment, then the efficacy declined to 63%–81% 35 days after treatment. No significant differences in the log mean number of fleas/dog were observed between the various formulations that contained Dowanol® PM after 35 days (p>0.05).

The permethrin formulation that contained only d-limonene exhibited an efficacy profile similar to that of the Dowanol® PM formulations but the efficacy declined to 88% after 4 weeks. The log mean number of fleas/dog that received permethrin in the d-limonene formulation was not significantly different (p >0.05) from the control 5 weeks after treatment.

In contrast, the initial efficacy of 65% permethrin in methyl carbitol (Defend® EXspot® Insecticide for Dogs) against fleas was approximately 90% 3 days after treatment. The efficacy against fleas was 96%–100% through 3 weeks after treatment. However, the log mean number of fleas/dog treated with 65% permethrin in methyl carbitol was not significantly (p >0.05) different from the control 4 weeks after treatment.

Lone star ticks (*Amblyomma americanum*) were exposed to the permethrin formulations for either 3 days (Day 3 count), 4 days (Day 7 count) or 5 days (day 14, 21 and 28 counts). As shown in Table 9, approximately 58% (range: 49%–65%) of ticks exposed to the various permethrin formulations were killed within 3 days. Nearly all ticks exposed to the various formulations for 4 or 5 days were killed for a 2 week period after the dogs were treated. The efficacy of the Dowanol® PM and d-limonene formulations declined to approximately 87% (range: 78%–94%) 3 weeks after treatment and further to approximately 62% (range: 45%–72%) 4 weeks after treatment.

The efficacy of the Dowanol® PM, Dowanol® PM/d-limonene 2:1 and Dowanol® PM/d-limonene 1:1 formulations against the lone star tick was 88%, 94% and 88%, respectively, 3 weeks after treatment. However, the efficacy of the Dowanol® PM and the Dowanol® PM/d-limonene 1:1 formulation was not significantly different from 90% 3 weeks after treatment.

The efficacy of the methyl Carbitol® formulation against the lone star tick after 4 days of tick exposure to the formulation of the dog (day 7 count) was 98%. The efficacy declined to 87% 2 weeks after dogs were treated. However, the 87% efficacy observed 2 weeks after dogs were treated was not significantly different (p >0.10) from 90%.

TABLE 9

| | % Efficacy (Lone Star Ticks) | | | | |
|---|---|---|---|---|---|
| Solvent | Day 3 | Day 7 | Day 14 | Day 21 | Day 28 |
| d-limonene | 65 | 96 | 97 | 88 | 46 |
| PM/d-l 1:2 | 59 | 99 | 91 | 78 | 64 |
| PM/d-l 1:1 | 61 | 98 | 95 | 88* | 59 |
| PM/d-l 2:1 | 57 | 97 | 87 | 94 | 68 |
| Dowanol ® PM | 56 | 95 | 98 | 88* | 72 |
| Methyl Carbitol | 49 | 98 | 87* | 78 | 8 |
| Control | (31) | (27) | (22) | (29) | (21) |

PM = Dowanol ® PM (propylene glycol monomethyl ether)
d-l = d-limonene
() - indicates the geometric mean number of parasites/control dog (n = 6)
*indicates the % efficacy is not significantly different from 90% (p > 0.10)

Example 5

This study compared, on dogs, the duration of efficacy of various insecticidal formulations, against the cat flea, *Ctenocephalides felis* and the brown dog tick, *Rhipicephalus sanguineus*, when applied as a spot on, under field use conditions.

Forty dogs of various breeding ranging in weight from 2.2 kg to 31.5 kg and both sexes were randomly assigned to four groups of ten dogs each. The four treatment groups were as follows:

65% permethrin in 35% Dowanol® PM (propylene glycol monomethyl ether)

Negative control: Untreated dogs

Positive control: Defend®EXspoto®(65% permethrin in methyl Carbitol)

65% permethrin in (1:1) 35% Dowanol PM® and d-limonene

One treatment application was made to each dog in Treatment Groups 1, 3 and 4 on Study Day 0. Each dog that weighed <15 kg received 1.0 mL of the Test formulation (topical spot on insecticide) applied to the skin of the dog's back between the shoulder blades. Each dog that weighed >15 kg received 2.0 mL of the Test formulation with 1.0 mL applied to the skin of the dog's back between the shoulder blades and 1.0 mL applied to the skin of the dog's back directly in front of the base of tail.

Dogs were infested with 100 unfed, adult fleas (both sexes) and with 50 unfed adult brown dog ticks (both sexes) on Study Days -5, -1, 5, 12, 19, 26, 33 and 40.

The fleas and ticks were counted and removed two days after treatment and weekly at two days following each infestation. Ticks were located, counted and removed from the dogs. Then, dogs were combed with an extra-fine flea comb and live fleas were removed and counted while combing each dog for at least five minutes or until no live fleas were found. The individuals performing flea and tick counts were "blinded" regarding the treatment group to which each dog was assigned. Blinding was assured by the use of two persons: one person brought the dog from the treatment groups for observations by the second person, the investigator.

The dogs' health was checked daily for signs of illness or adverse reactions. Treatment sites were observed at each infestation and count for signs of irritation.

Efficacy was determined using Abbott's formula (see Example 4). Results are shown in Tables 10 and 11.

TABLE 10

| Sol-vent | % Efficacy (Cat Fleas) | | | | | | |
|---|---|---|---|---|---|---|---|
| | Day 2 | Day 7 | Day 14 | Day 21 | Day 28 | Day 35 | Day 42 |
| PM[a] | 93.1 | 99.1 | 99.0 | 99.5 | 96.2 | 94.1 | 82.2 |
| Pm/d-l[b] 1:1 | 93.0 | 98.4 | 96.7 | 92.4 | 74.9 | 64.6 | — |
| MC[c] | 91.5 | 98.3 | 99.2 | 94.5 | 92.4 | 83.9 | 68.6 |

TABLE 11

| Sol-vent | % Efficacy (Brown Dog Ticks) | | | | | | |
|---|---|---|---|---|---|---|---|
| | Day 2 | Day 7 | Day 14 | Day 21 | Day 28 | Day 35 | Day 42 |
| PM[a] | 85.4 | 99.3 | 99.1 | 95.3 | 92.6 | 13.4 | 91.7 |
| Pm/d-l[b] 1:1 | 89.4 | 99.6 | 100 | 98.4 | 91.8 | 90.0 | 75.5 |
| MC[c] | 100 | 98.6 | 98.8 | 95.0 | 94.3 | 94.3 | 91.7 |

[a]propylene glycol monomethyl ether
[b]d-limonene
[c]methyl carbitol

The high order efficacy yielded by the combination solvent against fleas persisted through 21 days after treatment and declined unexpectedly between 21 and 28 days. Similarly in this example, the high order efficacy against the brown dog tick yielded by the combination solvent persisted through 35 days after treatment before gradually declining. The results shown in Tables 8–11 indicate that combination solvents for permethrin provide effective ectoparasite control in addition to advantages in cold solubility.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A parasiticidal composition for topical application to an animal consisting essentially of a pyrethroid or a pyrethrin and a carrier;
   wherein said carrier is selected from the group consisting of a terpene, a terpene derivative, a terpene with an alkyl glycol ether, and a terpene derivative with an alkyl glycol ether.

2. A parasiticidal composition for topical application to an animal consisting essentially of (i) a pyrethroid or a pyrethrin, (ii) a terpene or terpene derivative, and (iii) an alkyl glycol ether.

3. The composition of claim 1, wherein said terpene is d-limonene.

4. The composition of claim 1, wherein said alkyl glycol ether is selected from the group consisting of propylene glycol monomethyl ether, dipropylene glycol monoethyl ether, and diethylene glycol monomethyl ether.

5. The composition of claim 4, wherein said alkyl glycol ether is propylene glycol monomethyl ether.

6. The composition of claim 5, wherein said pyrethroid is permethrin.

7. The composition of claim 6, wherein said terpene is d-limonene.

8. The composition of claim 6, wherein said permethrin is present in an amount greater than 50% by weight of the total composition.

9. The composition of claim 8, wherein said permethrin is present in an amount of 65% by weight of the total composition.

10. The composition of claim 4, wherein said alkyl glycol ether is dipropylene glycol monomethyl ether.

11. The composition of claim 10, wherein said pyrethroid is permethrin.

12. The composition of claim 11, wherein said permethrin is present in an amount greater than 50% by weight of the total composition.

13. The composition of claim 12, wherein said terpene is d-limonene.

14. The composition of claim 13, wherein said permethrin is present in an amount of 65% by weight of the total composition.

15. The composition of claim 1, wherein said carrier is present in an amount from about 30% to about 70% by weight of said composition.

16. A parasiticidal composition for topical application to an animal consisting essentially of (I) permethrin, (ii) d-limonene, and (iii) propylene glycol monomethyl ether, wherein said permethrin is present in an amount greater than 50% by weight of the total composition.

17. The composition of claim 16, wherein said permethrin is present in an amount of 65% by weight of the total composition.

18. A method of controlling an ectoparasite infestation on an animal comprising topically administering to said animal the parasiticidal composition of claim 17.

19. The method of claim 18, wherein said animal is a dog.

20. A method of controlling an ectoparasite infestation on an animal comprising topically administering to said animal the parasiticidal composition of claim 2.

21. The method of claim 20, wherein said animal is a dog.

* * * * *

UNITED STATES PATENT AND TRADEMARK OFFICE
CERTIFICATE OF CORRECTION

PATENT NO.    : 6,660,768 B2
DATED         : December 9, 2003
INVENTOR(S)   : Richard G. Endris et al.

It is certified that error appears in the above-identified patent and that said Letters Patent is hereby corrected as shown below:

<u>Column 18,</u>
Line 23, replace "dipropylene glycol monoethyl ether" with -- dipropylene monomethyl ether --.

Signed and Sealed this

Tenth Day of January, 2006

JON W. DUDAS
*Director of the United States Patent and Trademark Office*